US009974477B2

(12) United States Patent
Cholette et al.

(10) Patent No.: US 9,974,477 B2
(45) Date of Patent: May 22, 2018

(54) QUANTIFICATION OF RENAL DENERVATION VIA ALTERATIONS IN RENAL BLOOD FLOW PRE/POST ABLATION

(71) Applicant: St. Jude Medical, Cardiology Division, Inc., St. Paul, MN (US)

(72) Inventors: Martin Cholette, Acton, CA (US); Sergio Shkurovich, Encino, CA (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 697 days.

(21) Appl. No.: 13/836,925

(22) Filed: Mar. 15, 2013

(65) Prior Publication Data

US 2014/0276124 A1    Sep. 18, 2014

(51) Int. Cl.
*A61B 5/00* (2006.01)
*A61B 5/01* (2006.01)
(Continued)

(52) U.S. Cl.
CPC .............. *A61B 5/4848* (2013.01); *A61B 5/01* (2013.01); *A61B 5/026* (2013.01); *A61B 5/201* (2013.01);
(Continued)

(58) Field of Classification Search
CPC ..... A61B 5/026; A61B 5/6852; A61B 5/6853; A61B 5/6855; A61B 5/6856; A61B 5/6857; A61B 5/6858; A61B 5/6859
See application file for complete search history.

(56) References Cited

U.S. PATENT DOCUMENTS 3,650,277 A    3/1972  Sjostrand et al.
4,411,266 A *  10/1983 Cosman ................. A61B 18/14
                                                              600/549
(Continued)

FOREIGN PATENT DOCUMENTS

WO    97/45157    12/1997
WO    00/66020    11/2000
(Continued)

OTHER PUBLICATIONS

Perel, Thermodilution technique to estimate cardiac output, 2009, Web, Retrieved from: http://www.anest.ee/public.filed.Cardiac %20output.pdf.*

(Continued)

*Primary Examiner* — Christian Jang
*Assistant Examiner* — Angeline Premraj
(74) *Attorney, Agent, or Firm* — Armstrong Teasdale LLP

(57) ABSTRACT

A renal denervation catheter includes a catheter shaft, at least one ablation member, and a sensor, and is operable to perform a renal denervation procedure. The catheter shaft includes a distal end portion insertable into a renal artery. The at least one ablation member is positioned at the distal end portion of the catheter shaft and operable to ablate renal nerves along a wall of the renal artery. The sensor provides information that correlates to blood flow in the renal artery. A change in blood flow rate in the renal artery resulting from the ablation is indicative of the efficacy of the renal denervation procedure.

8 Claims, 7 Drawing Sheets

(51) Int. Cl.
  *A61B 5/026* (2006.01)
  *A61B 18/14* (2006.01)
  *A61B 5/20* (2006.01)
  A61B 18/00 (2006.01)
  A61N 7/02 (2006.01)

(52) U.S. Cl.
  CPC ........ *A61B 5/6858* (2013.01); *A61B 18/1492* (2013.01); *A61B 2018/0088* (2013.01); *A61B 2018/00267* (2013.01); *A61B 2018/00404* (2013.01); *A61B 2018/00434* (2013.01); *A61B 2018/00511* (2013.01); *A61B 2018/00642* (2013.01); *A61B 2018/00714* (2013.01); *A61B 2018/00744* (2013.01); *A61B 2018/00791* (2013.01); *A61B 2018/00863* (2013.01); *A61B 2218/002* (2013.01); *A61N 7/022* (2013.01)

(56) References Cited

U.S. PATENT DOCUMENTS

| | | |
|---|---|---|
| 4,658,819 A | 4/1987 | Harris et al. |
| 5,035,694 A | 7/1991 | Kasprzyk et al. |
| 5,255,679 A | 10/1993 | Imran |
| 5,277,191 A * | 1/1994 | Hughes ............ A61B 5/029 |
| | | 600/505 |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 2001/0037048 A1* | 11/2001 | Pfeiffer ............ A61B 5/028 |
| | | 600/18 |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0255478 A1 | 10/2008 | Burdette |
| 2009/0076409 A1 | 3/2009 | Wu et al. |
| 2009/0137917 A1* | 5/2009 | Goedje ............ A61B 5/02028 |
| | | 600/526 |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2010/0312129 A1* | 12/2010 | Schecter ............ A61B 5/0031 |
| | | 600/508 |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0101413 A1 | 4/2012 | Beetel et al. |
| 2012/0143097 A1 | 6/2012 | Pike, Jr. |
| 2012/0143298 A1 | 6/2012 | Just et al. |
| 2012/0232409 A1 | 9/2012 | Stahmann et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |

(56) References Cited

FOREIGN PATENT DOCUMENTS

| WO | 2012/064818 | 5/2012 |
|---|---|---|
| WO | 2012/106492 | 8/2012 |

OTHER PUBLICATIONS

Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.

(56) References Cited

OTHER PUBLICATIONS

Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of the American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following *KSR V. Teleflex*, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.

(56) References Cited

OTHER PUBLICATIONS

Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(SUPPL.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Dibona, Gerald F, Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.

(56) References Cited

OTHER PUBLICATIONS

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of the American Heart Association, 1998;32:249-254.

Humpreys, Michael H., Renal Nerves and CKD: Is Renal Denervation the Answer?, Journal of The American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr., Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Zazgornik, Jan et al, Bilateral Nephrectomy: The Best, but Often Overlooked, Treatment for Refractory Hypertension in Hemodialysis Patients, AJH 1998; 11:1364-1370.

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.

Mogil, Robert A. et al, Renal Innervation and Renin Activity in Salt Metabolism and Hypertension, American Journal of Physiology, vol. 216, No. 4, Apr. 1969, 693-697.

Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Moss, Jonathan, Interventional Radiology and Renal Denervation, Interventions, vol. 13, Issue 3, 2013.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, A. et al, Selective Ablation of Porcine and Rabbit Liver Tissue Using Radiofrequency: Preclinical Study, European Surgical Research, 1999;31:371-379.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of the American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, Pace, vol. 18, Jun. 1995, 1236-1243.

Oparil, Suzanne et al, Renal Nerve Ablation: Emerging Role in Therapeutics; Blood Pressure, Oct. 2011, vol. 20, No. 5, pp. 253-255.

Oral, Hakan et al, Pulmonary Vein Isolation for Paroxysmal and Persistent Atrial Fibrillation, Circulation Journal of the American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Oz, Mehmet, Pressure Relief, TIME Magazine, Monday, Jan. 9, 2012.

Page, Irvine H. et al, Mechanisms, Diagnosis and Treatment of Hypertension of Renal Vascular Origin, Annal of Internal Medicine, Aug. 1959, vol. 51, No. 2, 196-211.

(56) References Cited

OTHER PUBLICATIONS

Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of the American Heart Association, Sep. 2012 ;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of the American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.

Blevins, Vibration of Structures Induced by Fluid Flow, Chapter 29, par 1, 2ed., Kreiger, Malibar, Fla. 1994.
Haller, et al., Evaluation of a new continuous thermodilution cardiac output monitor in critically ill patients: a prospective criterion standard study, Critical Care Medicine, May 1995, 23(5): 860-6.
DiBona et al., Effect of Renal Nerve Stimulation on the Responsiveness of the Rat Renal Vasculature, Am. J. Renal Physiology, vol. 283, F1056-F1065, 2002.
Le Fevre et al., Role of Angiotensin II in the Neural Control of Renal Function, Hypertension, 2003; 41:583-591.
PCT International Search Report for PCT International Application No. PCT/US2014/019513, dated May 16, 2014 (3 pp.).
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the SYMPLICITY HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.

(56) References Cited

OTHER PUBLICATIONS

Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/Jun.), 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/Pdf/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of The American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.

\* cited by examiner

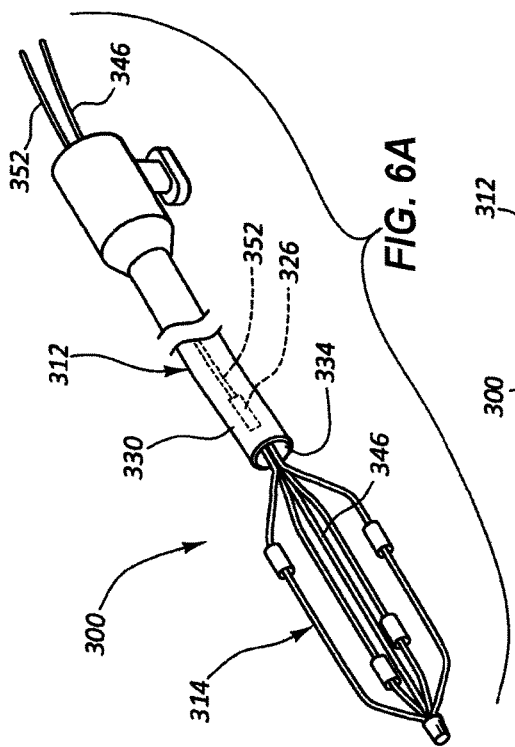
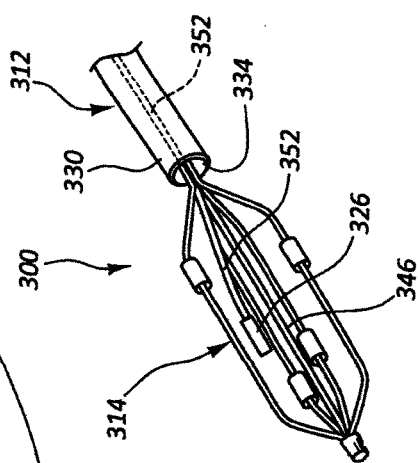
FIG. 6A
FIG. 6B
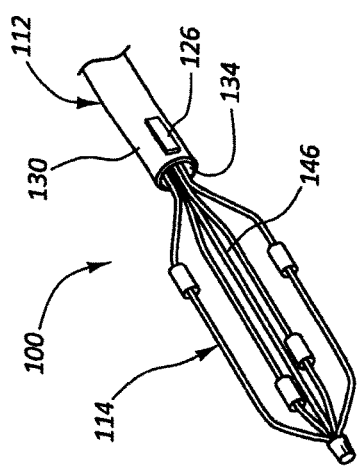
FIG. 4
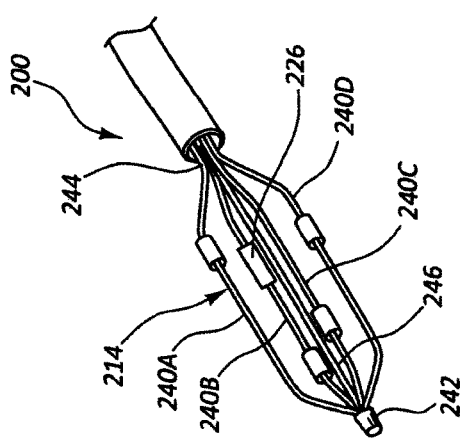
FIG. 5

QUANTIFICATION OF RENAL DENERVATION VIA ALTERATIONS IN RENAL BLOOD FLOW PRE/POST ABLATION

TECHNICAL FIELD

The present disclosure relates generally to renal denervation systems and methods, and more particularly, to systems and methods for assessing the efficacy of a renal denervation procedure at the time of the procedure.

BACKGROUND

Renal denervation is a method whereby amplified sympathetic activities are suppressed. Amplified sympathetic activities and their associated systems are known to contribute to arterial hypertension. Thus, renal denervation is used to treat hypertension or other cardiovascular disorders and chronic renal diseases.

Renal denervation is achieved through destruction of afferent and efferent nerve fibers that run adjacent to the renal artery. Renal denervation results in lower blood pressure in a patient. Renal denervation has also been shown to have benefits associated with treatment of heart failure, diabetes, obesity, sleep apnea, and ventricular tachycardia (VT). An established renal denervation procedure involves introducing a radiofrequency (RF) ablation catheter, which ablates renal nerves at various locations using variable energy. Presently, there is a need for feedback mechanisms to provide the operator with insight about the efficacy of the renal denervation treatment during the treatment procedure. This feedback would enable the operator to decide whether additional power and/or ablation locations are needed to accomplish adequate renal denervation.

SUMMARY

One aspect of the present disclosure relates to a renal denervation catheter having a catheter shaft, at least one ablation member, and a vibration sensor. The catheter shaft includes a distal end portion insertable into a renal artery. The at least one ablation member is positioned at the distal end portion of the catheter shaft and operable to ablate renal nerves through a wall of the renal artery. The vibration sensor is configured to measure vibrations in the renal denervation catheter prior to and after operating the at least one ablation member to ablate the renal nerves. A comparison of the measured vibrations is used to determine a change in blood flow rate in the renal artery resulting from the ablation.

The renal denervation catheter may include a cage structure positioned at the distal end portion of the catheter shaft, wherein the cage structure includes a plurality of radially spaced apart arms, and the at least one ablation member is positioned on at least one of the plurality of radially spaced apart arms. The plurality of radially spaced apart arms may converge at a distal tip, and the vibration sensor may be positioned at the distal tip. The vibration sensor may be positioned proximal of the at least one ablation member. An increase in blood flow rate may correlate with the efficacy of ablating with the at least one ablation member. The vibration sensor may be carried by a wire member insertable through a lumen of the catheter shaft. The at least one ablation member may include one of an ultrasound member and a radio frequency member.

Another aspect of the present disclosure relates to a method of determining efficacy of a renal denervation procedure in a renal artery. The method includes providing a renal denervation catheter having at least one ablation member and at least one vibration sensor, operating the at least one ablation member to provide renal denervation in the renal artery, measuring vibrations in the renal denervation catheter prior to and after providing the renal denervation, and comparing the measured vibrations to determine a change in blood flow rate through the renal artery as an indicator of efficacy of the renal denervation.

The renal denervation catheter may include a cage structure having a plurality of arms, wherein the at least one ablation member is positioned on one of the plurality of arms, and the at least one vibration sensor is positioned distal of the cage structure. The method may include positioning the at least one ablation member in contact with the renal artery prior to operating the at least one ablation member. The method may include correlating the measured vibrations to blood flow rates in the renal artery.

A further aspect of the present disclosure relates to a renal denervation catheter having a catheter shaft, at least one ablation member, and a temperature monitoring system. The catheter shaft has a distal end portion. The at least one ablation member may be positioned at a distal end portion of the catheter shaft and operable to provide renal denervation in a renal artery. The temperature monitoring system may include at least one temperature sensor and is configured to determine a change in temperature in a blood flow through the renal artery. The change in temperature correlates to a rate of blood flow.

The temperature monitoring system may include a fluid outlet to deliver a flow of fluid into the blood flow, and the at least one temperature sensor may be positioned downstream of the fluid outlet. The at least one ablation member may be configured to heat the blood flow, and the at least one temperature sensor may be positioned downstream of the at least one ablation member to monitor a temperature change of the blood flow. The temperature monitoring system may include a heating member positioned upstream of the at least one temperature sensor. The at least one ablation member may include one of an ultrasound member and a radio frequency member.

Another example method in accordance with the present disclosure relates to a method of determining efficacy of a renal denervation procedure in a renal artery. The method includes providing a renal denervation catheter having at least one ablation member and at least one temperature sensor, operating the at least one ablation member to provide denervation of renal nerves in the renal artery, measuring a temperature change in blood flow through the renal artery with the at least one temperature sensor prior to and after the denervation, and comparing the measured temperature changes to determine a change in blood flow rate through the renal artery as an indicator of efficacy of the denervation.

The method may include changing a temperature of the blood flow upstream of the at least one temperature sensor prior to measuring the temperature change. Changing a temperature of the blood flow may include injecting a flow of fluid having a temperature either above or below a temperature of the blood flow. Changing a temperature of the blood flow may include operating a heating element exposed to the blood flow. The heating element may include the at least one ablation member. The method may include stimulating the renal nerves prior to the denervation.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 4 is a perspective view of a distal end portion of another example embodiment of the renal denervation catheter of FIG. 1.

FIG. 5 is a perspective view of a distal end portion of another example embodiment of the renal denervation catheter of FIG. 1.

FIGS. 6A and 6B are perspective views of a distal end portion of another example embodiment of the renal denervation catheter of FIG. 1.

Throughout the drawings, identical reference numbers designate similar, but not necessarily identical, elements.

DETAILED DESCRIPTION

Figure 1:
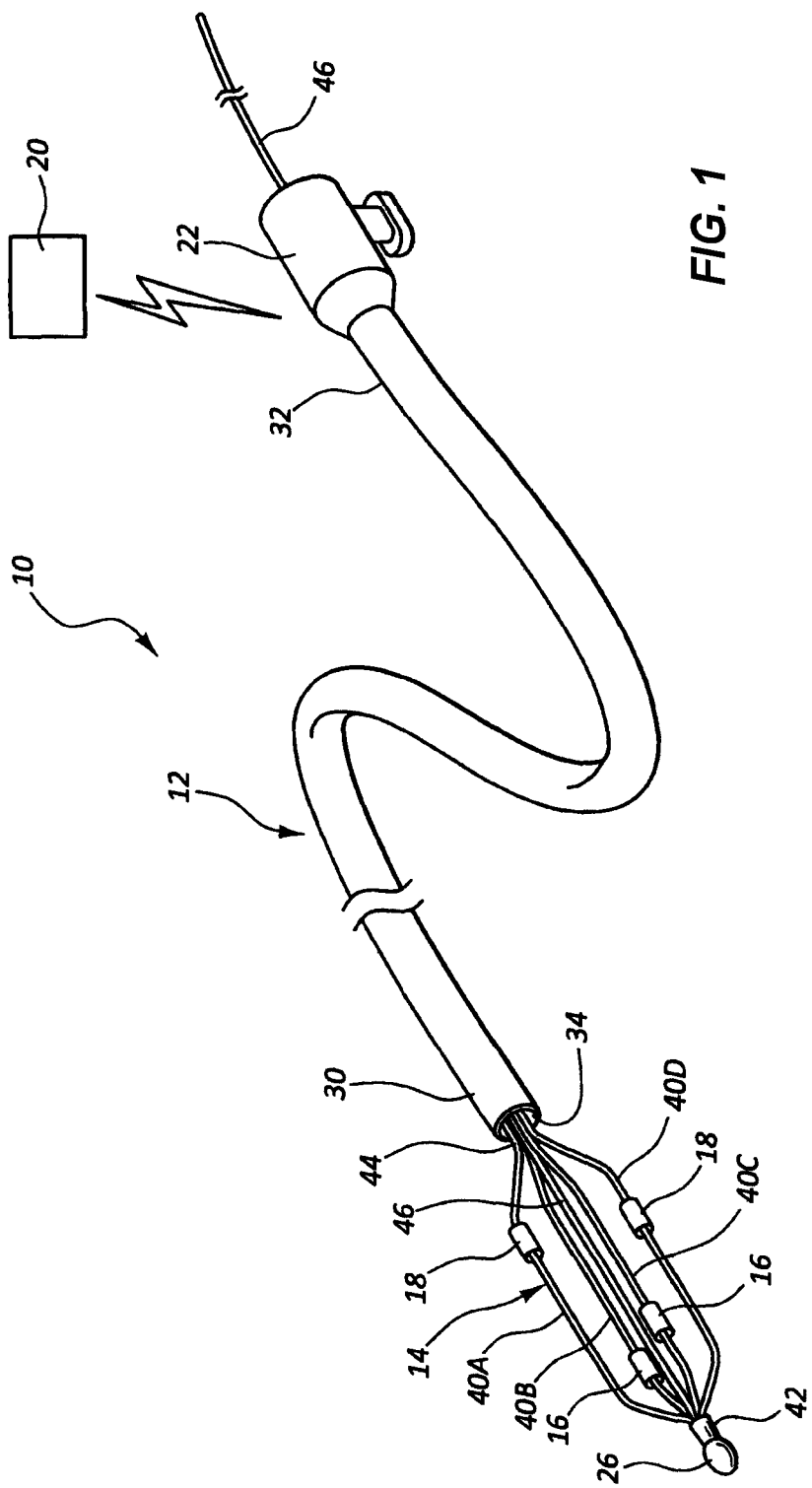
FIG. 1 is a perspective view of an example renal denervation catheter in accordance with the present disclosure.

The systems and methods disclosed herein are directed to aspects of renal denervation in a patient. The principles disclosed herein by be applicable to other systems and methods used for treating other aspects of the body, including, for example, any portion of the gastrointestinal, cardiovascular, nervous, hormonal, respiratory, excretory and reproductive systems of the body.

Renal denervation may involve ablation of the renal artery and associated renal nerves using an ablation catheter. While not meant to be limiting, the systems and methods disclosed herein are used to provide feedback to an operator concerning the efficacy of the renal denervation procedure. The feedback may be given during the procedure, such as after ablating the renal artery while the ablation catheter is still positioned within the renal artery.

The general structure and function of renal denervation catheters used for ablating tissue in the renal artery are known in the art. The principles disclosed herein may be useful in conjunction with various renal denervation catheters and methods of conducting renal denervation procedures.

The procedure for renal denervation may be relatively simple. An operator inserts a renal denervation catheter through an artery in the leg, into the aorta, and into the renal artery. In operation, the renal denervation catheter heats the arterial wall. The applied heat kills the renal nerves extending along an exterior and within a sidewall of the artery. The renal nerves typically are distributed in a random pattern along the renal artery. Consequently, the operator typically applies heat at multiple locations along the length of the renal artery and at different circumferential positions in order to have the best chance of ablating as many nerve fibers as needed for effective denervation.

Ablation may be done using, for example, radio frequency (RF) or ultrasound (US) energy. Other types of energy sources such as, for example, laser, cryothermal, and microwave energy sources may be used. Generally, the intent is to apply as much heat as necessary to kill the nerves, but no more than necessary in order to avoid damaging the renal artery.

The outcome of renal denervation is to reduce the kidneys' ability to secrete rennin and perform other functions that result in increased blood pressure. When the kidneys are sympathetically activated by the renal nerves, the kidneys secrete more rennin than they should, which leads to more angiotensin in the blood (e.g., resulting in an increase in blood pressure). By killing renal nerves, the renal denervation procedure is able to reduce or eliminate sympathetic activation of the renal nerves, reducing the kidneys' ability to secrete rennin and reducing instances of increased blood pressure.

An example renal denervation catheter includes a plurality of electrodes positioned circumferentially at different locations and arranged at spaced apart locations along a length of the catheter. In some arrangements, the electrodes may be carried by a basket or a cage structure having a plurality of arms or splines to which the electrodes are mounted. The basket or cage structure may be expandable to position the electrodes in contact with an inner surface of the renal artery. Traditionally, it has been difficult to know at the time of the renal denervation procedure whether sufficient amounts of energy have been applied at an appropriate number of locations to adequately ablate and kill the renal nerves. The present disclosure provides feedback mechanisms for the operator to determine whether sufficient denervation has taken place at the time of the procedure as opposed to waiting days or weeks after the procedure to determine whether sufficient denervation occurred during the procedure.

One way to provide the desired feedback is to stimulate the renal nerves prior to performing the ablation procedure, measure kidney functions, perform the ablation, stimulate the nerves after the ablation procedure, and measure kidney functions after the second stimulation. In one example, the stimulation may occur at a location adjacent to the ostium of the renal artery where the renal artery bifurcates from the aorta. The stimulation may be performed using the electrodes which are later used to ablate the renal nerves. The stimulation may be applied at several axial and circumferential positions in the renal artery to increase the reliability of the stimulation (e.g., aligning one or more electrode in proximity to one or more nerves in order to effectively stimulate the nerve). Ablation may occur at separate locations along the length of the renal artery from where stimulation is provided. Ablation may be applied at multiple circumferential and axial positions in the renal artery. The electrodes may be repositioned a plurality of times within the renal artery to provide the desired stimulations and ablations. Multiple series of stimulating, measuring and ablating may be used to confirm efficacy of the denervation procedure. Further, there may not be direct communication between any specific electrodes during, for example, any of the stimulations performed.

One measurable output of the kidneys resulting from the stimulation is a decrease in glomerular filtration rate (GFR), which decreases the renal blood flow (e.g., decreases the amount of blood that is flowing through the renal artery). The flow rate through the renal artery may be determined using at least one of, for example, vibrations and thermodilution, which will be described in further detail below.

By monitoring the change in rate of blood flow through the renal artery using the example blood flow measuring procedures discussed herein (e.g., vibration and thermodilution) an operator is able to indirectly determine whether the renal denervation procedure was successful while the renal denervation catheter remains positioned within the renal artery. In accordance with the present disclosure, a measurable change in renal blood flow will result in response to a successful renal denervation procedure. By determining whether an appropriate change in blood flow has occurred using the exemplary techniques disclosed herein, the system may provide real-time feedback or at least feedback within the time frame of a renal denervation procedure, as to the efficacy of the renal denervation procedure. Using techniques for determining rates of flow through a conduit (e.g., vibration and thermodilution), desired feedback concerning the efficacy of the renal denervation procedure may be provided, as will be described in further detail below.

Figure 3:
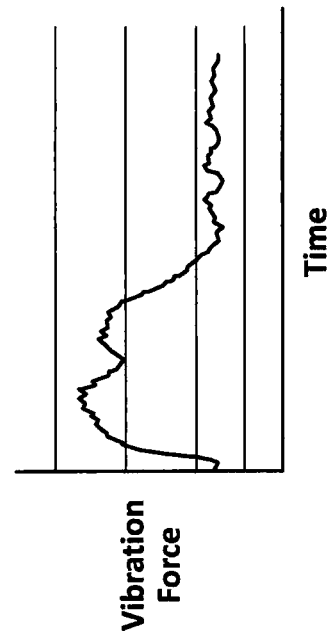
FIG. 3 is a graph showing change in vibration force in the renal denervation catheter of FIG. 1 in response to change of fluid flow.
Figure 2:
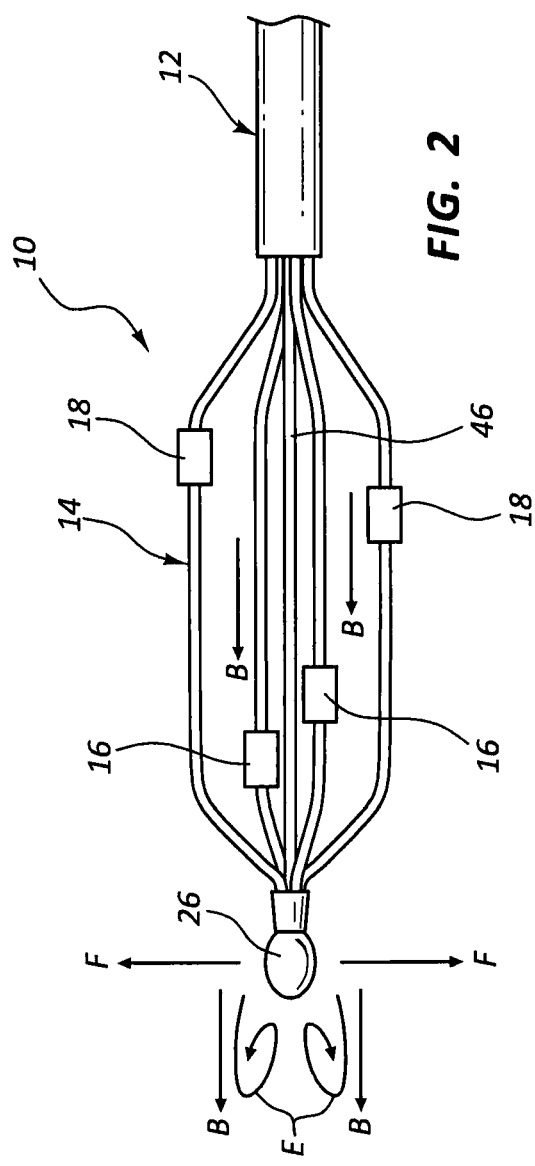
FIG. 2 is a detailed view of a distal end portion of the renal denervation catheter of FIG. 1.

Referring now to FIGS. 1-3, an example renal denervation catheter 10 is shown and described in detail. The renal denervation catheter 10 includes a catheter shaft 12, a deployable basket 14, distal and proximal electrodes 16, 18, a controller 20, and a hub 22. A vibration sensor 26 may be positioned, for example, at a distal end of the deployable basket 14.

The catheter shaft 12 may include distal and proximal ends 30, 32 and a lumen 34. The deployable basket 14 may include a plurality of splines or arm members 40A-40D, distal and proximal ends 42, 44, and a pull wire 46. Operating the pull wire 46 may move the deployable basket 14 from a retracted position to a deployed or expanded position, as shown in FIGS. 1 and 2. The deployable basket 14 in the expanded position shown in FIGS. 1 and 2 may position the ablation electrodes 16, 18 in direct contact with an inner surface of a renal artery. A separate one of the splines 40A-40D may support at least one of the ablation electrodes 16, 18. In other arrangements, multiple electrodes may be positioned on a single spline. Alternatively, additional splines beyond the number of ablation electrodes 16, 18 may be used.

The controller 20 may control operation of the ablation electrodes 16, 18 and the vibration sensor 26. The controller 20 may receive feedback from the ablation electrodes 16, 18 and vibration sensor 26 as part of determining efficacy of a renal denervation procedure (e.g., determining a change in blood flow through the renal artery). The controller 20 may be directly wired to the ablation electrodes 16, 18 and vibration sensor 26. Alternatively, the controller 20 may have wireless communications with various sensors and electronic components of the renal denervation catheter 10.

The pull wire 46 may extend through the lumen 34 of the catheter shaft 12. A proximal portion of the pull wire 46 may be accessible by an operator to actuate the deployable basket 14 between the retracted and expanded positions.

The vibration sensor 26 may be positioned at the distal end 42 of the deployable basket 14. The vibration sensor 26 may provide an output signal related to vibration force. The output signal may be plotted over time as shown in the graph of FIG. 3. FIG. 3 shows a reduction in vibration force after the flow rate is reduced. The vibrations may be induced in the vibration sensor 26 from blood flow around the vibration sensor 26. As blood circulates through the deployable basket 14, the flow is distributed and becomes turbulent around the tip of the deployable basket 14. The vibrations are related to the speed of the blood, and thus the blood flow rate. Equations correlating vibrations induced in a structure positioned in a flow of fluid are described in Brevins, R. D., "Vibration of Structures Induced by Blood Flow," chapter 29, part 1, 2d ed., Kreiger, Malibar, Fla., 1994. 13, which is incorporated herein in its entirety by this reference.

An equation for determining vibration induced force (F) provided by Brevins is as follows:

$$F = \tfrac{1}{2}\pi U^2 C_L D L J \sin(2\pi f_s t) \quad \text{(Equation 1)}$$

Where:
$\rho$=fluid density
U=fluid velocity
$C_L$=lift coefficient (a function of Reynolds number and cylindrical motion)
D=diameter
L=length of cylinder
J=joint acceptance
$f_s$=frequency of alternating lift force
t=time
and joint acceptance (J) is determined as follows:
J=1 (if fully correlated along entire length L)
$J=(l_c/L)^{1/2}$ (if $l_c$ (spanwise correlation length)<<L)

FIG. 2 shows a blood flow B moving through the deployable basket 14 and around the vibration sensor 26. Positioning the renal denervation catheter 10 within blood flow through the renal artery may create turbulence in the blood flow B. The turbulence may be evidenced by eddy currents E downstream of the vibration sensor 26. The vibration forces F may occur in a plurality of direction such as in a lateral direction shown in FIG. 2. Providing at least some asymmetrical features on the renal denervation catheter 10 may induce additional turbulence that may be more easily measured by the vibration sensor 26. Some asymmetrical features include, for example, positioning of the ablation electrodes 16, 18 at various circumferential and axial positions along the deployable basket 14. Alternatively, varying the shape, size and orientation of the splines 40A-40D may create additional asymmetry.

The vibration sensor 26 may be located at various locations on the renal denervation catheter. For example, FIG. 4 shows a vibration sensor 126 positioned on a catheter shaft 112 at a location proximal of a deployable basket 114 of a renal denervation catheter 100. The vibration sensor 126 may be positioned at a distal end portion 130 of the catheter shaft 112, which may be operated using a pull wire 146. The vibration sensor 126 may be positioned on an outer circumferential surface of the catheter shaft 112. Alternatively, the vibration sensor 126 may be positioned internally within a lumen 134 of the catheter shaft 112.

FIG. 5 shows another example renal denervation catheter 200 having a vibration sensor 226 mounted to one of the splines 240A-240D of a deployable basket 214. The deployable basket 214 may be operated using a pull wire 246. The vibration sensor 226 may be positioned at an axial location space between the distal and proximal ends 242, 244 of the deployable basket 214. In at least one example, the sensor measurements taken by vibration sensor 226 may occur prior to expansion of the deployable basket 214 into the expanded position shown in FIG. 5 to avoid contact with the inner surface of the renal artery which may otherwise affect operation of the vibration sensor 226. Alternatively, the deployable basket 214 may be operated into the expanded position shown in FIG. 5 prior to taking the vibration measurements of vibration sensor 226. In another embodiment, the vibration sensor 226 may be mounted to the pull wire 246 used to operate the deployable basket 214 between expanded and retracted positions.

In an alternative arrangement, a vibration sensor 326 may be mounted to a separate carrier wire 352 as shown in FIGS. 6A and 6B. The carrier wire 352 may position the vibration sensor 326 within a lumen 334 of a catheter shaft 312 as shown in FIG. 6A. In one example, the vibration sensor 326 is positioned adjacent to a distal end 330 of the catheter shaft 312. The carrier wire 352 may position the vibration sensor 326 proximal of a deployable basket 314. The deployable basket 314 may be operated using the pull wire 346.

FIG. 6B shows the carrier wire 352 advanced distally to position the vibration sensor 326 outside of the catheter shaft 312. The vibration sensor 326 may be positioned radially inward from the splines of the deployable basket 314. In other arrangements, the carrier wire 352 may be advanced further distally to position the vibration sensor 326 distal of the deployable basket 314. The carrier wire 352 may be a commercially available product such as the PressureWire™ Certus available from St. Jude Medical of St. Paul, Minn.

Figure 7:
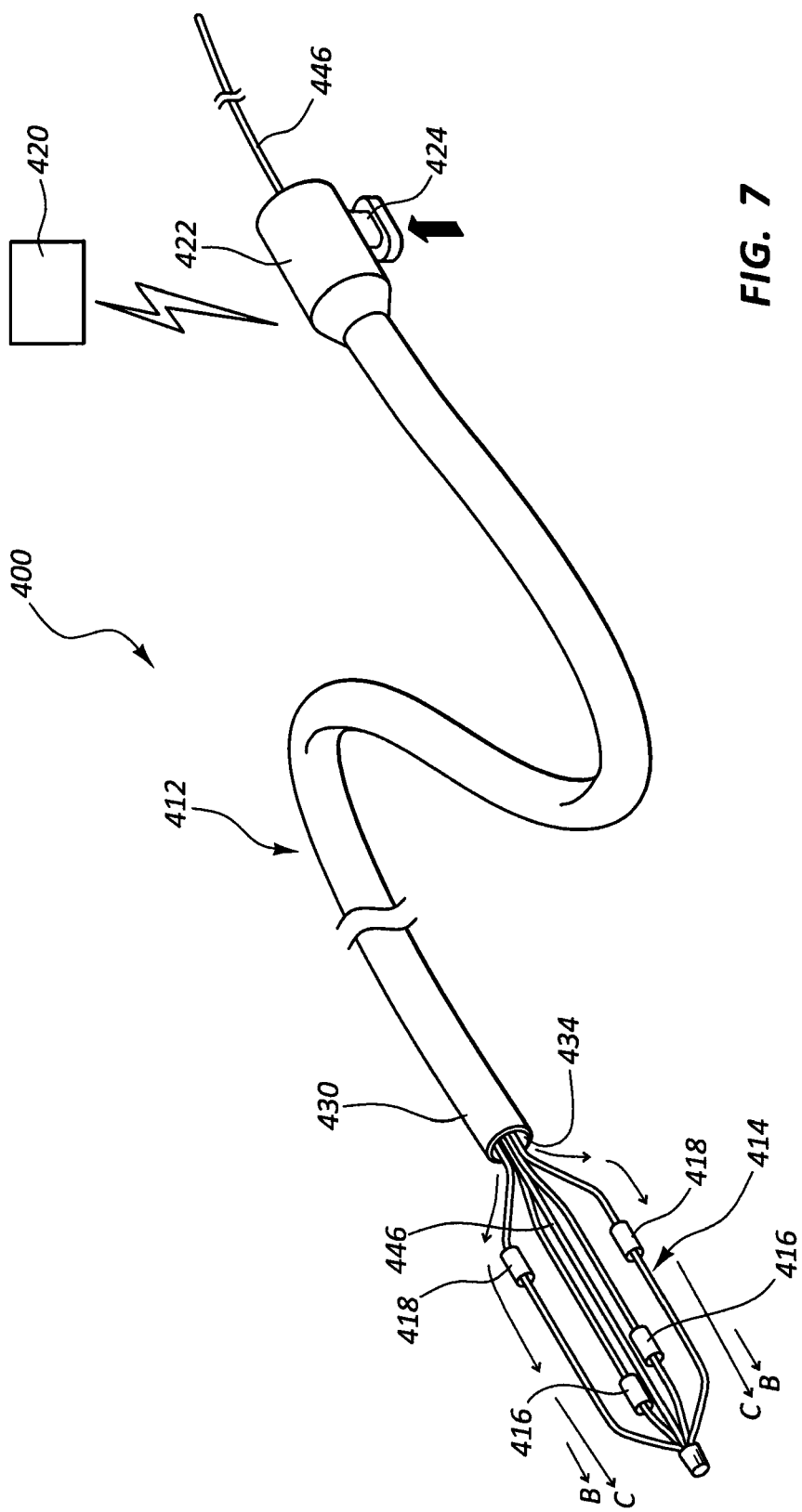
FIG. 7 is a perspective view of another example renal denervation catheter in accordance with the present disclosure.
Figure 8:
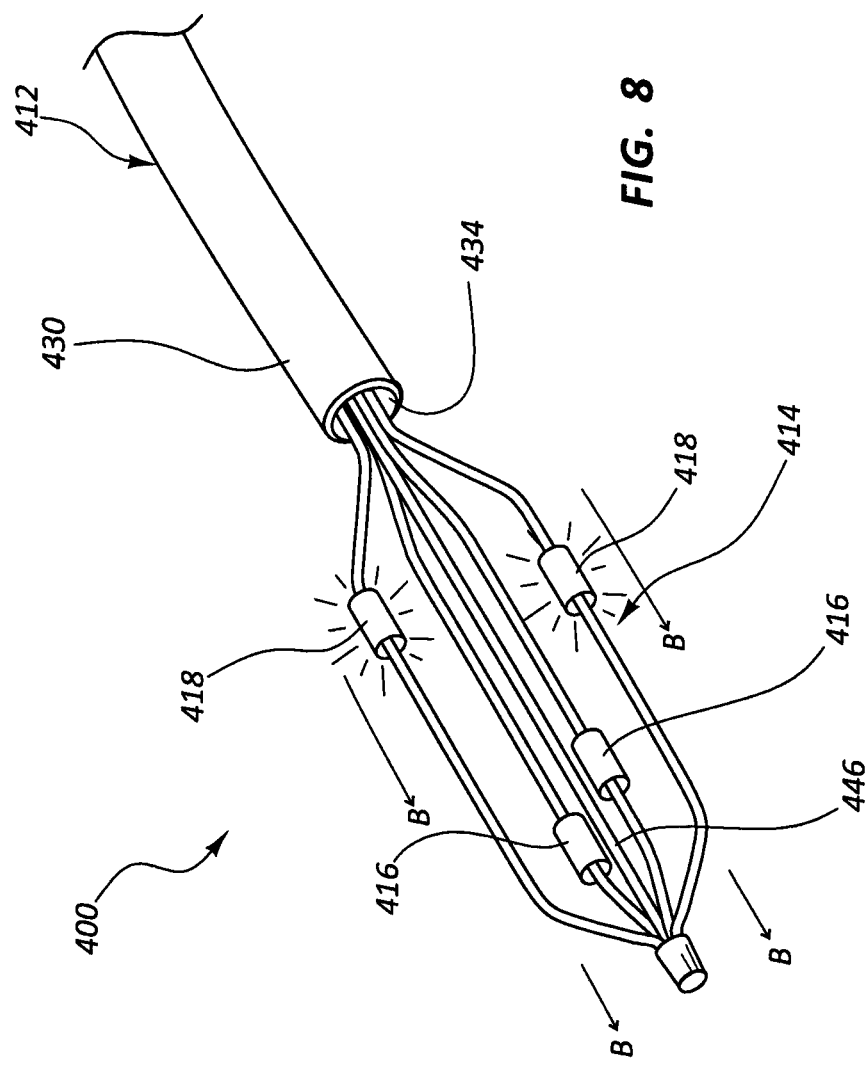
FIG. 8 is a perspective view of a distal end portion of another example embodiment of the renal denervation catheter of FIG. 7.

Referring now to FIGS. 7 and 8, thermodilution techniques are described as an alternative option for determining change of blood flow through a renal artery. Thermodilution may be adapted to measure blood flow in the renal artery using the heating electrodes and thermistors present on the renal denervation catheter, or provide injection of cold saline through a dedicated port in the renal denervation catheter along with using the thermistors for a temperature gradient measurement. The thermodilution techniques may have the additional advantage of providing a status of renal blood flow pre-ablation (e.g., without first providing electrical stimulation to the renal nerves) and comparing the pre-ablation flow with post-ablation flow to determine whether the ablation procedure altered renal blood flow.

FIG. 7 shows a renal denervation catheter 400 having a catheter shaft 412, a deployable basket 414, distal and proximal ablation electrodes 416, 418, a controller 420, and a hub 422 having a fluid port 424. The catheter shaft 412 may include a lumen 434 dedicated to delivery of a saline or other liquid provided at a predetermined temperature. The lumen 434 may be used for delivery of a pull wire 446, which is used to operate the deployable basket 414. The saline is delivered into the lumen 434 via the fluid port 424 and ejected at a distal end 430 of catheter shaft 412 as a fluid flow C. The fluid flow C mixes with the blood flow B. At least one of the distal and proximal electrodes 416, 418 includes a thermistor configured to monitor the temperature of fluid flow around the electrode. Typically, a profile of temperature monitored by the thermistor of the distal and proximal electrodes 416, 418 is proportional to the rate of blood flow. Thus, based on the temperature profile, a calculation may be made of the blood flow needed to dilute the temperature from the temperature of the injected saline to a level sensed by the thermistor. Typically, the temperature of the injected saline and the distance downstream of the thermistor from the point of injecting the saline into the blood flow are used to provide an accurate calculation.

A number of known methods have been used to determine cardiac output using saline thermodilution as discussed above. Some examples of such known methods are discussed in Haller, et al., "Evaluation of a new continuous thermodilution cardiac output monitor in critically ill patients: a prospective criterion standard study," Critical Care Medicine, May 1995, 23(5):860-6, which is incorporated herein in its entirety by this reference.

Another example thermodilution technique is described with reference to FIG. 8. In FIG. 8, the renal denervation catheter 400 provides heating of the blood flow B using a heating element of at least one of the proximal electrodes 418. A thermistor of at least one of the distal electrodes 416 may be used to monitor a temperature of the blood flow B. The system of FIG. 8 provides changing a temperature of the blood flow using at least one of the electrodes instead of changing of the temperature of the blood flow by injecting a cold fluid as described above with reference to FIG. 7. In one example, both of the proximal electrodes 418 are used to heat the blood flow B, and both of the distal electrodes 416 are used to measure the temperature of the blood B. Inputs used for determining the change of blood flow prior to and after a renal denervation procedure in which the renal nerves are ablated may include an amount of heat generated by the proximal electrodes 418 (e.g., during operation at a predetermined setting), a change in temperature of the blood flow B over time, and a separation distance between the distal and proximal electrodes 416, 418.

Typically, each of the distal and proximal electrodes 416, 418 of the renal denervation catheter 400 include a heating element and a thermistor. The heating element and thermistor may be included as part of an ablation electrode such that the operator may have real-time feedback concerning the temperature of the heating element to avoid application of excessive heat to the tissue of the renal artery.

Each of the renal denervation catheters 10, 100, 200, 300, 400 described above with reference to FIGS. 1-8 may operate to determine change of blood flow prior to, during, and after an ablation procedure in which renal nerves associated with the renal vessel are ablated or killed. In some examples, it is possible for the blood flow rate to change abruptly at some point during the ablation procedure when enough of the nerve fibers are killed. The devices and methods disclosed herein may provide feedback concerning change in blood flow rate independent of electrical stimulation of the renal nerves prior to, during and after a renal denervation procedure.

Figure 9:
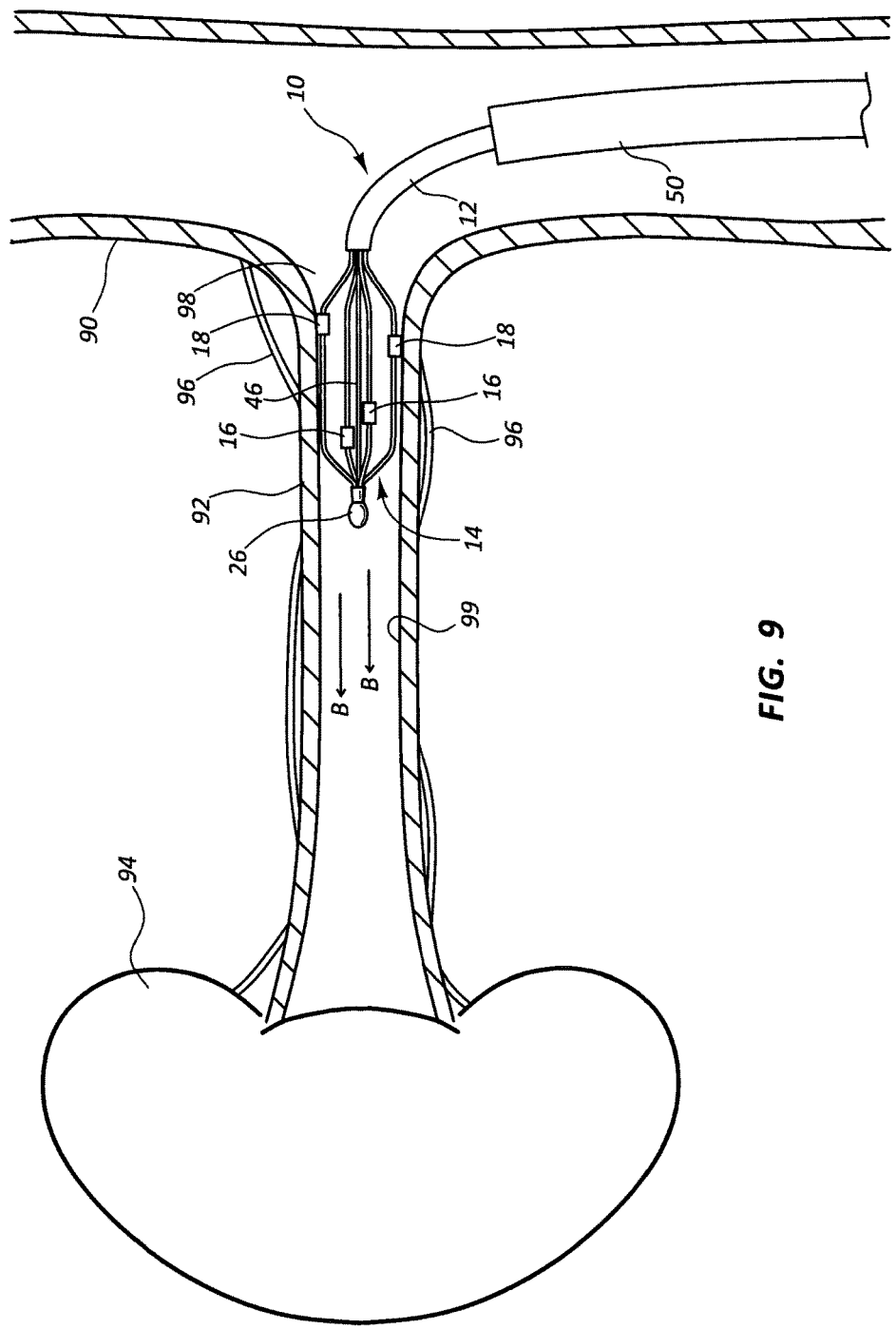
FIG. 9 shows the renal denervation catheter of FIG. 1 inserted into a renal artery and arranged to stimulate renal nerves.
Figure 10:
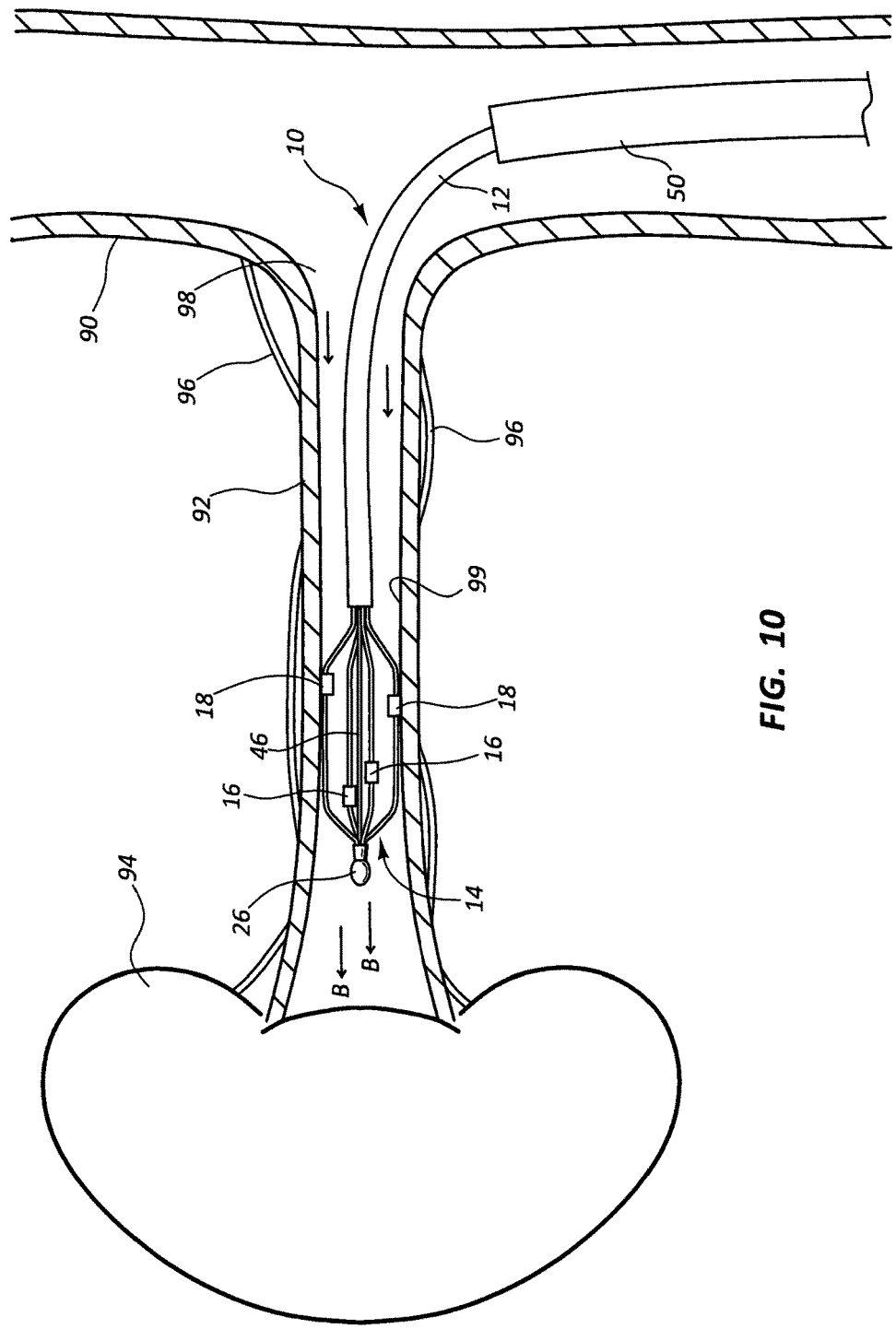
FIG. 10 shows the renal denervation catheter of FIG. 1 positioned within the renal artery and arranged to ablate the renal nerves.

Referring now to FIGS. 9 and 10, an example method of renal denervation is described. FIG. 9 shows a renal denervation catheter 10 advanced through an introducer 50 and into a renal artery 92. The renal denervation catheter 10 extends through an ostium 98 where the renal artery 92 branches from the aorta 90. The deployable basket 14 is positioned within the renal artery 92 adjacent to the ostium 98. The deployable basket 14 is operated into an expanded position to contact the ablation electrodes 16, 18 with an inner surface 99 of the renal artery 92. The ablation electrodes 16, 18 are operated to provide electrical stimulation of a plurality of renal nerves 96 positioned within and along an exterior of the renal artery 92. The electrical stimulation may create a response from kidney 94 in the form of, for example, an increase or decrease of rennin production.

After stimulating the renal nerves, the renal denervation catheter 10 may be further advanced into a position in the renal artery 92 spaced distally from the ostium 98, as shown in FIG. 10. The vibration sensor 26 may be used to determine vibration forces in the renal denervation catheter 10.

The vibration forces may be correlated to a rate of blood flow B in the renal artery 92.

The renal denervation catheter 10 may then be operated to ablate the renal nerves 96 by producing heat with the ablation electrodes 16, 18. The amount of heat generated by the ablation electrodes 16, 18 may depend on a number of factors including, for example, the number and location of the ablation electrodes 16, 18, a position within the renal artery 92, and the size of the renal artery 92.

The vibration sensor 26 may be used again to determine the rate of blood flow B. The system may provide a comparison of the rate of blood flow B before and after the ablation. If the change in blood flow exceeds a certain threshold amount or the absolute value of the blood flow reaches a predetermined level, the ablation may be considered successful. If more ablation is needed, the ablation electrodes 16, 18 may be operated repeatedly to produce more heat to ablate the renal nerves 96.

In a further treatment step, the renal denervation catheter 10 may be moved proximally to reposition the deployable basket 14 at the ostium 98 as shown in FIG. 9. The renal nerves 96 may be electrically stimulated a second time using, for example, at least one of the ablation electrodes 16, 18 as described above with reference to FIG. 9. The electrical stimulation may generate a response in the kidney 94, such as an increase or decrease in rennin production. If the ablation procedure described with reference to FIG. 10 was efficacious, the second electrical stimulation may create little or no response in the kidney 94. The renal denervation catheter 10 may be withdrawn from the renal artery 92 if the renal denervation procedure is determined to be complete.

In some examples, the renal denervation catheter 10 may maintain a constant position while stimulating the renal nerves prior to ablation, measuring blood flow prior to ablation, ablating the renal nerves, stimulating the renal nerves after ablation, and measuring blood flow after the second stimulation. Furthermore, a predetermined time delay may be used between each of the stimulation, ablation, and flow determination steps described above with reference to FIGS. 9 and 10. The deployable basket 14 may be moved between expanded and retracted positions between each of the stimulation, ablation, and flow rate determination steps, and between moving the renal denervation catheter 10 between various axial positions (e.g., as shown in FIGS. 9 and 10).

In other examples, the denervation methods described with reference to the figures may be done without the steps of stimulating the renal nerves 96 before or after measuring the blood flow using vibration sensor 26, measuring blood flow via a change in blood flow temperature using the ablation electrodes 16, 18, and ablating the renal nerves 96 with the ablation electrodes 16, 18.

An example method of determining the efficacy of a renal denervation procedure in a renal artery may include providing a renal denervation catheter having at least one ablation member and at least one vibration sensor. The at least one ablation member may be operated to provide renal denervation in the renal artery (e.g., ablating renal nerves through the sidewall of the renal artery). The renal denervation catheter may measure vibrations induced by blood flow through the renal artery. The vibrations may correlate to a rate of blood flow through the renal artery. The blood flow prior to and after operating the ablation member to provide renal denervation may be compared to determine whether sufficient ablation has occurred to denerve the renal nerves of the renal artery.

The vibrations may be measured using a vibration sensor positioned at any desired location along a length of the renal denervation catheter. For example, the vibration sensor may be positioned at a distal most tip of the renal denervation catheter. In other examples, the vibration sensor may be positioned along a deployable basket of the renal denervation catheter, along a catheter shaft at a location proximal of the deployable basket, or on a separate carrier wire moveable independent of the catheter shaft and the deployable basket.

Another example method of determining efficacy of a renal denervation procedure in a renal artery includes providing a renal denervation catheter having at least one ablation member and at least one temperature sensor. The method includes determining a temperature change in the blood flow prior to and after operating the at least one ablation member to ablate renal nerves associated with the renal artery. The temperature changes are correlated to a blood flow rate through the renal artery. The blood flow rates are used as an indicator of efficacy of the denervation procedure.

The temperature of the blood flow may be changed prior to or after the ablation procedure by supplying a flow of cold saline at a location upstream of at least some of the ablation members. In another example, at least some of the ablation members themselves are used to heat the blood flow and others of the ablation members include a temperature sensor (e.g., a thermistor) to measure a temperature of the blood flow. These and other methods may be used in accordance with the disclosure provided herein.

Generally, the systems and methods disclosed herein may provide feedback to an operator concerning the efficacy of a renal denervation procedure using changes in blood flow through the renal artery. The change in blood flow may be determined using a comparison of blood flow rates measured before and after ablating the renal artery and associated renal nerves. The change in blood flow may be determined using an absolute change in blood flow rate associated with ablating the renal artery.

As used in this specification and the appended claims, the terms "engage" and "engagable" are used broadly to mean interlock, mesh, or contact between two structures or devices. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A renal denervation catheter, comprising:
    a catheter shaft having a distal end portion comprising a deployable basket including a plurality of splines;
    at least one ablation member positioned on a spline of the deployable basket and configured to provide renal denervation in a renal artery; and
    a temperature monitoring system having at least one temperature sensor and configured to calculate a rate of a blood flow through the renal artery based on i) a temperature of a thermal source, wherein the thermal source is configured to increase a temperature of the blood flow and wherein the thermal source is the at least one ablation member, ii) a blood flow temperature measured by the at least one temperature sensor, wherein the measured blood flow temperature is based on operation of the thermal source exposed to the blood flow, and iii) a distance between the thermal source and the at least one temperature sensor, and wherein the deployable basket is expanded or retracted based on performing renal denervation or operating the temperature monitoring system.

2. The renal denervation catheter of claim 1, wherein the at least one ablation member is further configured to provide renal nerve stimulation.

3. The renal denervation catheter of claim 1, wherein the at least one temperature sensor is positioned on a spline of the deployable basket and downstream of the at least one ablation member to monitor a temperature change of the blood flow.

4. The renal denervation catheter of claim 1, wherein the at least one ablation member comprises one of an ultrasound member and a radio frequency member.

5. A method of determining efficacy of a renal denervation procedure in a renal artery, comprising:
   providing a renal denervation catheter having at least one ablation member and at least one temperature sensor;
   operating the at least one ablation member to provide denervation of renal nerves along the renal artery;
   changing a temperature of blood flow upstream of the at least one temperature sensor by operating a thermal source exposed to the blood flow, wherein the thermal source is configured to increase the temperature of blood flow;
   determining a blood flow rate through the renal artery prior to and after the denervation based on i) a temperature of the thermal source, wherein the thermal source is the at least one ablation member, ii) a blood flow temperature measured by the at least one temperature sensor, wherein the measured blood flow temperature is based on the operation of the thermal source exposed to the blood flow, and iii) a distance between the thermal source and the at least one temperature sensor; and
   determining a change in the blood flow rate through the renal artery as an indicator of efficacy of the denervation.

6. The method of claim 5, wherein the at least one ablation member and the at least one temperature sensor are positioned on a deployable basket.

7. The method of claim 6, further comprising expanding the deployable basket prior to the denervation and retracting the deployable basket prior to the changing a temperature of blood flow.

8. The method of claim 5, further comprising stimulating the renal nerves prior to the denervation.

* * * * *